(12) United States Patent
Mailhe et al.

(10) Patent No.: US 11,908,047 B2
(45) Date of Patent: Feb. 20, 2024

(54) GENERATING SYNTHETIC X-RAY IMAGES AND OBJECT ANNOTATIONS FROM CT SCANS FOR AUGMENTING X-RAY ABNORMALITY ASSESSMENT SYSTEMS

(71) Applicant: Siemens Healthcare GmbH, Erlangen (DE)

(72) Inventors: Boris Mailhe, Plainsboro, NJ (US); Florin-Cristian Ghesu, Skillman, NJ (US); Siqi Liu, Princeton, NJ (US); Sasa Grbic, Plainsboro, NJ (US); Sebastian Vogt, Monument, CO (US); Dorin Comaniciu, Princeton Junction, NJ (US); Awais Mansoor, Potomac, MD (US); Sebastien Piat, Lawrence Township, NJ (US); Steffen Kappler, Effeltrich (DE); Ludwig Ritschl, Buttenheim (DE)

(73) Assignee: Siemens Healthineers AG, Forchheim (DE)

( * ) Notice: Subject to any disclaimer, the term of this patent is extended or adjusted under 35 U.S.C. 154(b) by 321 days.

(21) Appl. No.: 17/249,735

(22) Filed: Mar. 11, 2021

(65) Prior Publication Data

US 2022/0292742 A1    Sep. 15, 2022

(51) Int. Cl.
*G06T 11/00* (2006.01)
*G06T 3/40* (2006.01)
*G06T 7/11* (2017.01)
*G06T 7/00* (2017.01)
*G16H 30/40* (2018.01)

(52) U.S. Cl.
CPC .......... *G06T 11/008* (2013.01); *G06T 3/4053* (2013.01); *G06T 7/0012* (2013.01); *G06T 7/11* (2017.01); *G06T 2207/10081* (2013.01); *G06T 2207/20081* (2013.01);
(Continued)

(58) Field of Classification Search
CPC ....... G06T 7/11; G06T 3/4053; G06T 7/0012; G16H 30/00
See application file for complete search history.

(56) References Cited

U.S. PATENT DOCUMENTS 7,653,226 B2    1/2010 Guhring et al.
10,803,354 B2 * 10/2020 Zhao ...................... A61B 6/03
(Continued)

FOREIGN PATENT DOCUMENTS

WO    WO-2018048507 A1 *  3/2018 ........... A61B 5/0035
WO    WO-2020198854 A1 * 10/2020

OTHER PUBLICATIONS

Li et al., "Digitally reconstructed radiograph generation by an adaptive Monte Carlo method," 2006, Physics in Medicine & Biology, vol. 51, No. 11, pp. 2745-2752.
(Continued)

*Primary Examiner* — John Villecco
*Assistant Examiner* — Courtney Joan Nelson (57) ABSTRACT

Systems and methods for generating a synthetic image are provided. An input medical image in a first modality is received. A synthetic image in a second modality is generated from the input medical image. The synthetic image is upsampled to increase a resolution of the synthetic image. An output image is generated to simulate image processing of the upsampled synthetic image. The output image is output.

20 Claims, 7 Drawing Sheets

(52) U.S. Cl.
CPC .......... *G06T 2207/20084* (2013.01); *G06T 2211/408* (2013.01); *G16H 30/40* (2018.01)

(56) References Cited

U.S. PATENT DOCUMENTS

2020/0311913 A1* 10/2020 Soni .............. G16H 30/40
2020/0311932 A1* 10/2020 Hooper .......... G06F 18/2413
2021/0342638 A1* 11/2021 Ghesu ............ G06N 20/00

OTHER PUBLICATIONS

Bhat et al., "Accelerated Digitally Reconstructed Radiograph Generation Scheme for 2D to 3D Image Registration of Vertebrae Based on Sparse Sampling and Multi-Resolution," 2017, 2017 Ninth International Conference on Advanced Computing (ICoAC), pp. 51-57.

Ragte et al., "A novel approach for fast generation of digitally reconstructed radiographs to increase the automation of PD-3D registration system," 2016, 2016 IEEE International Conference on Recent Trends in Electronics, Information & Communication Technology (RTEICT), pp. 1869-1872.

Mori et al., "Development of a GPU-based multithreaded software application to calculate digitally reconstructed radiographs for radiotherapy," 2009, Radiological Physics and Technology, vol. 2, pp. 40-45.

Zhu et al., "Unpaired Image-to-Image Translation using Cycle-Consistent Adversarial Networks," 2017, Proceedings of the IEEE International Conference on Computer Vision (ICCV), pp. 2223-2232.

Utility U.S. Appl. No. 15/929,427, filed May 1, 2020.

European Patent Application No. 20166951.2, filed Mar. 31, 2020.

* cited by examiner

GENERATING SYNTHETIC X-RAY IMAGES AND OBJECT ANNOTATIONS FROM CT SCANS FOR AUGMENTING X-RAY ABNORMALITY ASSESSMENT SYSTEMS

CROSS-REFERENCE TO RELATED APPLICATIONS

This application claims the benefit of U.S. Provisional Application No. 63/041,372, filed Jun. 19, 2020, the disclosure of which is herein incorporated by reference in its entirety.

TECHNICAL FIELD

The present invention relates generally to generating synthetic x-ray images and object annotations from CT (computed tomography) images, and in particular to generating synthetic x-ray images and object annotations from CT images for augmenting x-ray abnormality assessment systems.

BACKGROUND

Machine learning based systems have recently been proposed for automatically performing various medical imaging analysis tasks, such as, e.g., lesion detection, organ segmentation, etc., on x-ray images. Such machine learning based systems are trained on large datasets of annotated x-ray images. Typically, the x-ray images are manually annotated by a radiologist reading the x-ray images. However, the ambiguity of the x-ray images caused by the 2D projection of the x-ray beams results in a high number of missed or incorrect annotations. Accordingly, acquiring large datasets of annotated x-ray images is challenging.

A DRR (digitally reconstructed radiograph) is a simulation of an x-ray image generated from CT (computed tomography) images. However, DRRs have a significantly lower resolution as compared to real x-ray images due to the lower resolution of the CT images and filtering commonly applied to CT images. Accordingly, the resolution and appearance of DRRs is not comparable to x-ray images and therefore DDRs are not sufficient for training machine leaning based systems for performing medical imaging analysis tasks on x-ray images.

BRIEF SUMMARY OF THE INVENTION

In accordance with one or more embodiments, systems and methods for generating high quality and realistic synthetic images are provided. An input medical image in a first modality is received. A synthetic image in a second modality is generated from the input medical image. The synthetic image is upsampled to increase a resolution of the synthetic image. An output image is generated to simulate image processing of the upsampled synthetic image. The output image is output.

In one embodiment, the synthetic image is upsampled by performing a first upsampling of the synthetic image to increase a one-dimensional resolution of the synthetic image in a head-feet dimension using a first trained machine learning based model and performing a second upsampling of the synthetic image to increase a two-dimensional resolution of the synthetic image using a second trained machine learning based model.

In one embodiment, the output image is generated using a trained machine learning based model. The trained machine learning based model may be trained using unpaired training images.

In one embodiment, the synthetic image is generated by segmenting an anatomical object of interest from the input medical image, masking regions of the input medical image outside of the segmented anatomical object of interest, and generating the synthetic image from the masked input medical image.

In one embodiment, the first modality is CT (computed tomography) and the second modality is x-ray. The synthetic image may be generated by generating a DRR (digitally reconstructed radiograph) from the input medical image.

In one embodiment, the input medical image comprises annotations. Generating the synthetic image may comprise translating the annotations to correspond to the synthetic image and upsampling the synthetic image may comprise resampling the translated annotations to the resolution of the upsampled synthetic image.

In one embodiment, one or more additional synthetic images in the second modality are generated from the input medical image. The upsampling, the generating the output image, and the outputting steps are repeated for each respective additional synthetic image of the one or more additional synthetic images using the respective additional synthetic image as the synthetic image to generate a plurality of output images.

In one embodiment, a machine learning based model for performing a medical imaging analysis task is trained based on the output image These and other advantages of the invention will be apparent to those of ordinary skill in the art by reference to the following detailed description and the accompanying drawings.

DETAILED DESCRIPTION

The present invention generally relates to methods and systems for generating synthetic x-ray images and object annotations from CT images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for the generation of high-quality and realistic synthetic x-ray images. Such synthetic x-ray images are generated by generating DRRs (digitally reconstructed radiographs) from CT (computed tomography) images. The DRRs are upsampled to a resolution similar to that of real x-ray images. The upsampled DRRs are then input into a machine learning based model to generate output x-ray images to thereby simulate image processing commonly performed on real x-ray images by an x-ray image acquisition device. Advantageously, the synthetic x-ray images generated in accordance with embodiments described herein may be utilized for training machine learning based models for performing medical imaging analysis tasks on real x-ray images.

Figure 1:
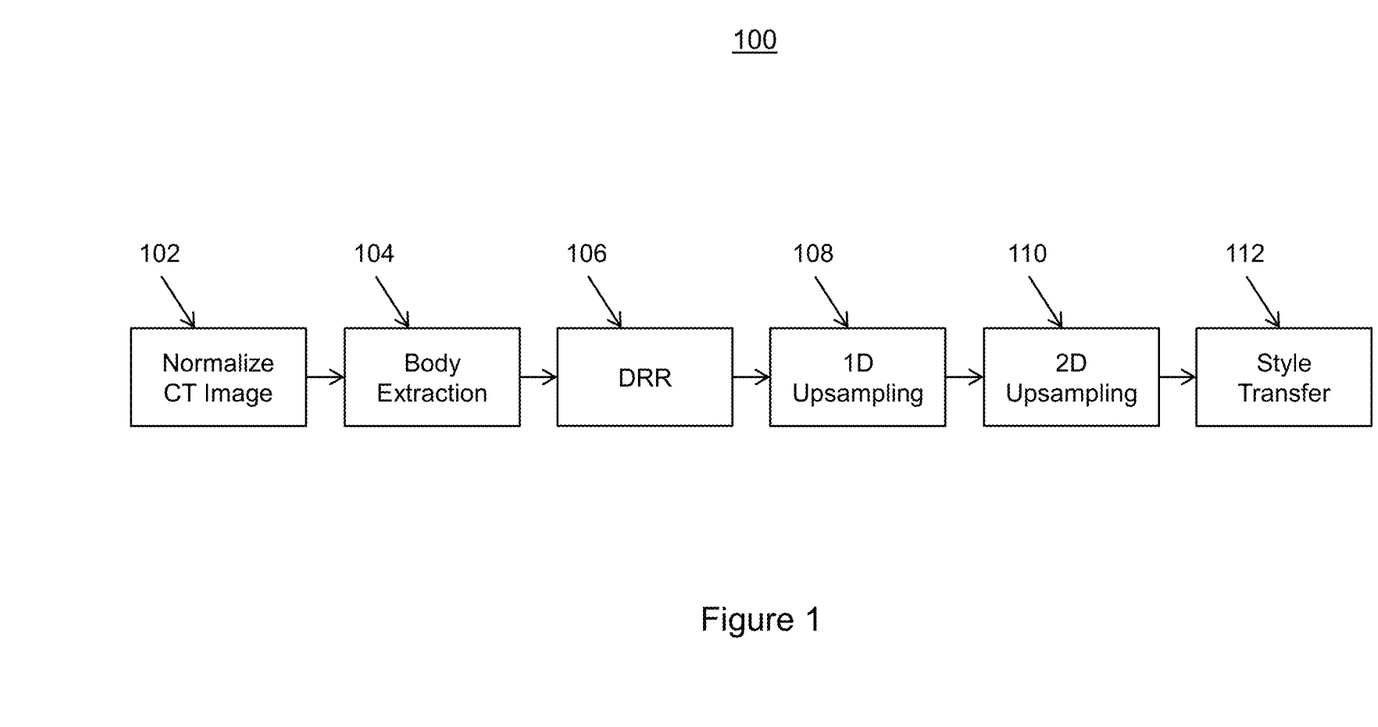
FIG. 1 shows a workflow for generating synthetic x-ray images, in accordance with one or more embodiments.
Figure 2:
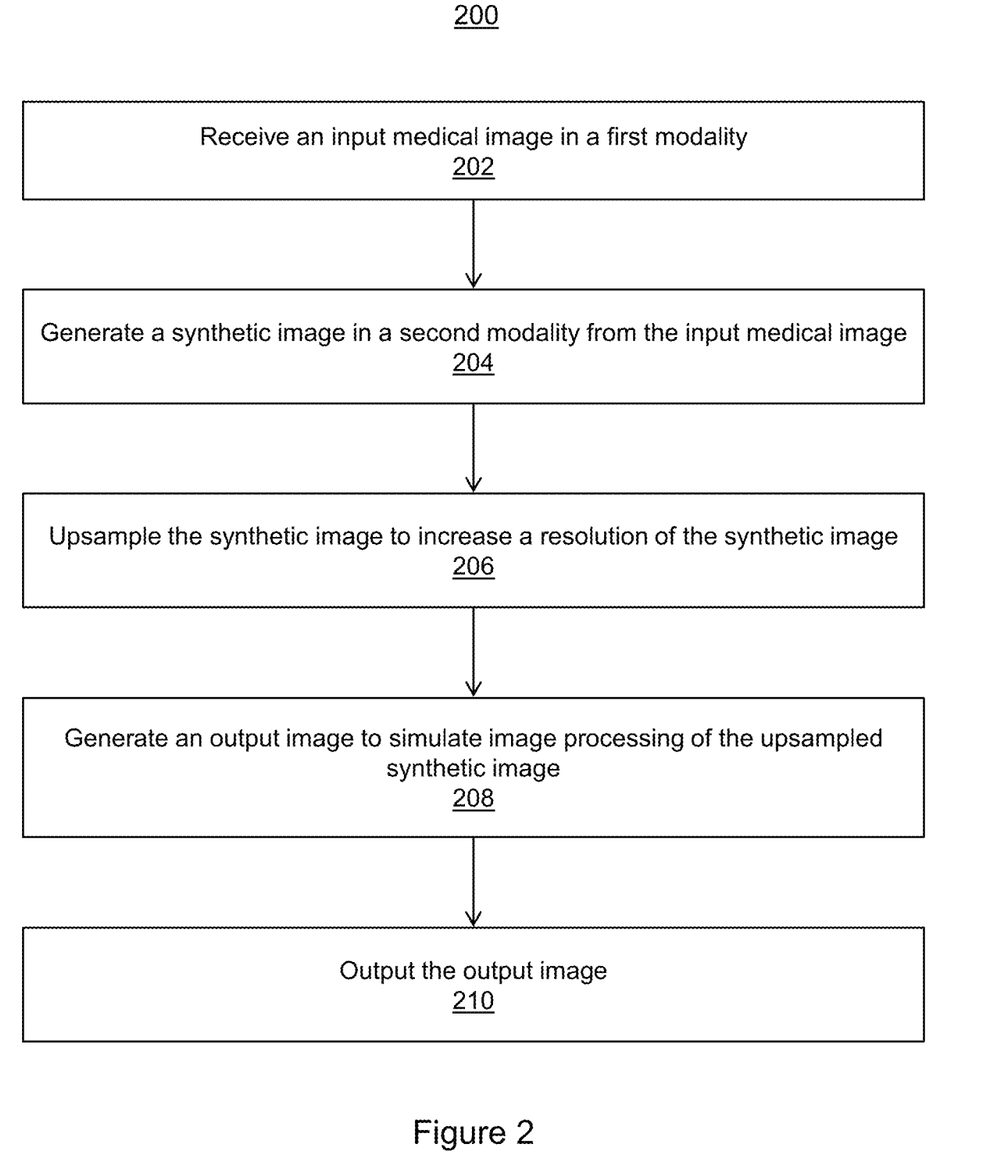
FIG. 2 shows a method for generating an output image in one modality from an input medical image in another modality, in accordance with one or more embodiments.

FIG. 1 shows a workflow 100 for generating synthetic x-ray images, in accordance with one or more embodiments. FIG. 2 shows a method 200 for generating an output image in one modality from an input medical image in another modality, in accordance with one or more embodiments. FIG. 1 and FIG. 2 will be described together. The steps of method 200 may be performed by one or more suitable computing devices, such as, e.g., computer 702 of FIG. 7.

At step 202, an input medical image in a first modality is received. The input medical image may be of any anatomical object of interest of a patient, such as, e.g., one or more organs, bones, lesions or nodules, etc. In one example, the input medical image is an image of a chest of a patient showing one or more pulmonary nodules. The input medical image may be annotated to identify items of interest, such as, e.g., the location of the lungs or of the pulmonary nodules.

In one embodiment, the first modality is CT. However, the first modality may be any other suitable modality, such as, e.g., MRI (magnetic resonance imaging), ultrasound, x-ray, or any other medical imaging modality or combinations of medical imaging modalities. The input medical image may be a 2D (two dimensional) image or a 3D (three dimensional) volume, and may comprise a single input medical image or a plurality of input medical images (e.g., a sequence of images acquired over time). The input medical image may be received directly from an image acquisition device, such as, e.g., a CT scanner, as the medical image is acquired, or can be received by loading a previously acquired medical image from a storage or memory of a computer system or receiving a medical image that has been transmitted from a remote computer system.

At step 204, a synthetic image in a second modality is generated from the input medical image. In one embodiment, the second modality is x-ray. However, the second modality may be any other suitable modality, such as, e.g., CT, MRI, ultrasound, or any other medical imaging modality or combinations of medical imaging modalities. The synthetic medical image is a translation of the input medical image from the first modality to the second modality.

In one embodiment, where the first modality is CT and the second modality is x-ray, the synthetic image may be a DRR. While DRRs are simulations of x-ray images, the DRRs have a lower resolution as compared to x-ray images and do not have the image processing commonly applied to x-ray images by x-ray acquisition devices. As shown in FIG. 1, to generate the DRR, an input CT medical image is (optionally) normalized at block 102 and a body (or any other anatomical object of interest) of the patient is extracted from the normalized input CT medical image at block 104. The body extraction is performed to remove foreign objections in the normalized input CT medical image to be consistent with x-ray images. For example, a table that the patient is lying on, which is not shown in a typical x-ray image, may be removed from the normalized input CT medical image. The body of the patient may be extracted from the normalized input CT medical image by segmenting the body from the normalized input CT medical image, e.g., using a pre-trained machine learning based segmentation model. The regions of the normalized input CT medical image outside of the segmented body are then masked. A DRR is generated from the masked normalized input CT medical image at block 106. The DRR may be generated by projecting the masked normalized input CT medical image using Beer's law to simulate the physical x-ray travelling through tissue. The geometry of the simulated x-ray may be defined by a user (e.g., clinician) for generating the DRR. In one example, the simulated x-ray may be in a posterior-anterior geometry, which is representative of outpatient x-ray acquisitions of a patient in a standing position. In another example, the simulated x-ray may be in an anterior-posterior geometry, which is representative of inpatient x-ray acquisitions of a patient in a supine position. In one embodiment, the DDR may be generated as described in U.S. Pat. No. 7,653,226, issued Jan. 26, 2010, the disclose of which is incorporated herein by reference in its entirety. Any other suitable technique for generating the DRR may also be applied.

Figure 3:
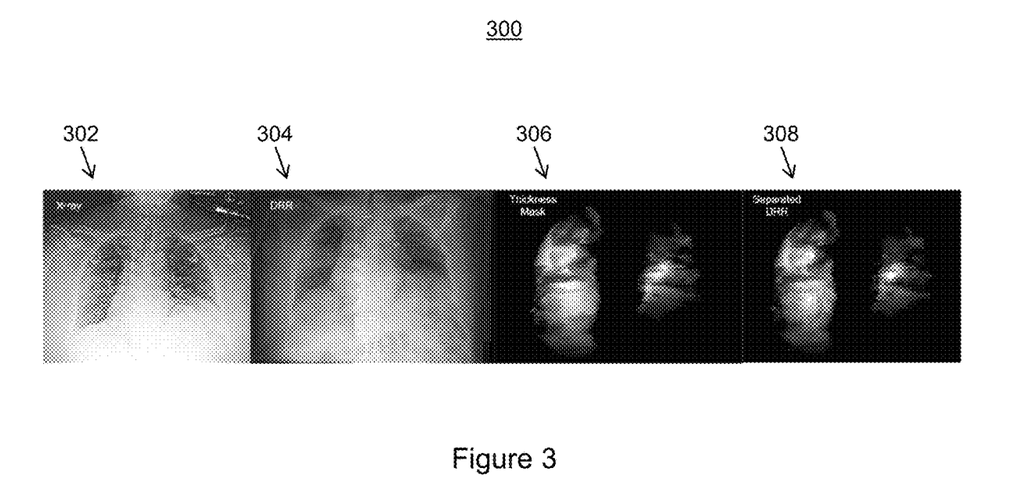
FIG. 3 shows a comparison of a real x-ray image with images generated in accordance with one or more embodiments.

In one embodiment, where the input medical image is annotated, the annotations may be translated to correspond to the synthetic image. For example, a DRR may be calculated for the annotations themselves, resulting in a 2D map of the thickness of the annotated anatomical structures. In another example, the input medical image may be masked based on the annotations, resulting in a separated DRR map comprising a plurality of separate layers each showing contribution by different annotated anatomical structures. Thickness maps allow for the direct evaluation of 3D measurements (e.g., volumes) from 2D DRRs. Separated DRR maps allow for the estimation of the relative contribution of an anatomical structure for each pixel of the DRR, which correlates with the visibility of the anatomical structure in the DRR. An example of a thickness map and a separated DRR map are shown in FIG. 3, described in further detailed below.

At step 206 of FIG. 2, the synthetic image is upsampled to increase a resolution of the synthetic image. In order to accommodate the slice resolution variability in CT protocols, the upsampling is split into two components: 1D upsampling and 2D upsampling. For example, as shown in FIG. 1, a 1D upsampling of the synthetic image is performed at block 108 and a 2D upsampling of the synthetic image is performed at block 110.

In the 1D upsampling, a first upsampling of the synthetic image is performed to increase a 1D resolution of the synthetic image in a head-feet dimension using one or more machine learning based models, thereby resulting in the synthetic image having isotropic resolution (i.e., equal resolution in all dimensions). The head-feet dimension is typically the dimension with the lowest resolution in a CT image (typically the z resolution in the coordinate system of the CT scanner) due to the stacking of 2D slices along the travel-direction of the scanner table. The in-plane resolution of the axial 2D slices (typically the x-y resolution in the coordinate system of the CT scanner) is typically higher and determined (among other criteria) by the size of the scanner's detector element. The 1D upsampling decreases the spatial size of voxels in the head-feet dimension to increase the resolution in the head-feet dimension, thereby addressing the difference in the z resolution versus the x-y resolution. In one embodiment, the machine learning based models for 1D upsampling are trained during a prior offline or training stage to upsample an image by integer factors between, e.g., 2 and 4. Once trained, the trained machine learning based models are applied to the synthetic image during an online or testing stage (e.g., at step 206 of FIG. 2) using the integer factor closest to the anisotropy of the synthetic image. In one embodiment, the trained machine learning based models for 1D upsampling is a 2D CNN (convolutional neural networks). However, the machine learning based models for 1D upsampling may comprise any other suitable machine learning based model.

In the 2D upsampling, a second upsampling of the synthetic image (as upsampled according to the 1D upsampling) is performed to increase a 2D resolution of the synthetic image using one or more machine learning based models, thereby increasing the overall resolution of the synthetic image to a target resolution. In one embodiment, the machine learning based models for 2D upsampling is a machine learning based super resolution network trained during a prior offline or training stage using supervised training based on matching low resolution/high resolution pairs. The low resolution/high resolution pairs may be generated by retrospective downsampling of real x-ray images. Once trained, the trained machine learning based models are applied to the synthetic image during an online or testing stage (e.g., at step 206 of FIG. 2). The machine learning based models for 2D upsampling may comprise any suitable machine learning based model.

In one embodiment, where synthetic image includes annotations, the annotations may also be resampled to the same resolution as the upsampled synthetic image by linear interpolation.

At step 208, an output image is generated to simulate image processing of the upsampled synthetic image. In one example, an output image is generated by performing a style transfer at block 112 of FIG. 1. The generation of the output image simulates the image processing commonly applied to x-ray images by the x-ray acquisition device, bringing the image impression of the upsampled synthetic image similar to that of typical x-ray images. For example, such simulated image processing may include adjustments to image quality attributes such as, e.g., non-linear contrast correction, (CLAHE) contrast-limited adaptive histogram equalization, sharpening, denoising, etc.

Figure 4:
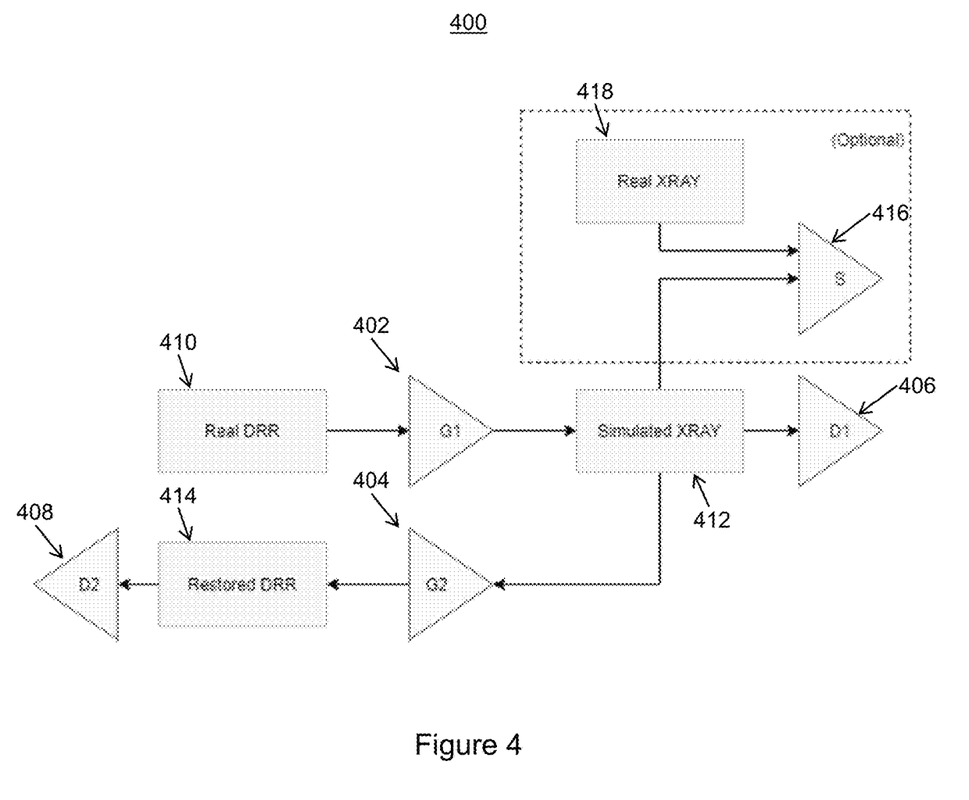
FIG. 4 shows an exemplary network architecture of a Cycle GAN (generative adversarial network), in accordance with one or more embodiments.

The output image may be generated using any suitable technique. In one embodiment, the output image is generated from the upsampled synthetic image using a machine learning based model. The machine learning based model may be trained using unmatched pairs of training images with unsupervised learning approach, due to the inability to obtain matching pairs of x-ray images and DRRs. In one example, the machine learning based model is a Cycle GAN (generative adversarial network). An illustrative network architecture of a Cycle GAN is shown in FIG. 4, described in detail below. However, the machine learning based model may be any other suitable machine learning based model. In another embodiment, the output image is generated from the upsampled synthetic image by spectral normalization.

At step 210, the output image is output. For example, the output image can be output by displaying the output image on a display device of a computer system, storing the output image on a memory or storage of a computer system, or by transmitting the output image to a remote computer system.

In one embodiment, annotations associated with the output image are output with the output image.

In one embodiment, the output image is utilized to train a machine learning based model for performing a medical imaging analysis task, such as, e.g., lesion detection and assessment, organ segmentation, etc.

In one embodiment, step 204 may be performed for a plurality of iterations each using different parameters for generating one or more additional synthetic images in the second modality from the input medical image for synthetic data augmentation. For example, one or more additional DRRs may be generated by augmenting the geometry of the simulated x-ray by, e.g., varying the source to detector distance, the source to object distance, or the center ray orientations. Steps 206-210 may be repeated for each respective additional synthetic image of the one or more additional synthetic images using the respective additional synthetic image as the synthetic image to generate a plurality of different output images. The same variations may be applied to the annotations to obtain matching ground truth projections. Accordingly, better visibility of certain structures may be achieved that would otherwise be occluded. The different output images would positively impact the learning process when used to train machine learning based models for performing medical imaging analysis tasks.

FIG. 3 shows a comparison of a real x-ray image with images generated in accordance with one or more embodiments. Image 302 shows a real x-ray image. Image 304 shows an output image generated in accordance with method 200 of FIG. 2 from a CT image acquired from the same patient within 48 hours. Image 306 shows a thickness mask of a lesion. Image 308 shows a separate DRR map of the lesion.

FIG. 4 shows an exemplary network architecture 400 of a Cycle GAN, in accordance with one or more embodiments. The Cycle GAN may be applied at step 208 of FIG. 2 to generate the output image. As shown in FIG. 4, network architecture 400 comprises a pair of generators G1 402 and G2 404 and a pair of discriminators D1 406 and D2 408. Generators G1 402 and G2 404 and discriminators D1 406 and D2 408 may be implemented using one or more CNNs or any other suitable machine learning based model.

The Cycle GAN is trained during a prior offline or training stage using unpaired real x-ray and DRR training images. At acquisition, image processing was applied to the real x-ray images by the x-ray image acquisition device to facilitate viewing. The Cycle GAN is trained generate a synthetic x-ray image from a DRR to simulate the image processing commonly applied to real x-ray images. Generator G1 402 is trained to generate simulated x-ray 412 from real DRR 410 and generator G2 404 is trained to generate a restored DRR 414 from the simulated x-ray 412. Generators G1 402 and G2 404 are trained with adversarial loss using discriminators D1 406 and D2 408. Discriminator D1 406 aims to distinguish between simulated x-ray 412 and a real x-ray (not shown) and discriminator D2 408 aims to distinguish between restored DRR 414 and a real DRR (not shown). Accordingly, discriminators D1 406 and D2 408 guide generators G1 402 and G2 404 to respectively generate realistic synthetic x-ray images and DRRs that are indistinguishable from the real x-ray images and the real DRRs.

In one optional embodiment, the Cycle GAN comprises segmentation network 416. Segmentation network 416 ensures that objects of interest (e.g., lesions) in real DRR 310 are preserved in the simulated x-ray 412. As shown in FIG. 4, segmentation network 416 segments an object of interest from simulated x-ray 412 and an object of interest from real x-ray 418. The results of the segmentations are compared to guide generator G1 402 to generate synthetic x-ray images that preserve the object of interest.

Once trained, generator G1 402 is applied during an online or testing stage (e.g., at step 208 of FIG. 2) to generate a synthetic x-ray image from a DRR image. Generator G2 404 and discriminators D1 406 and D2 408 are not utilized during the online stage. In one embodiment, segmentation network 416 may be utilized to segment an object of interest from the output image for further processing (e.g., to perform additional medical imaging analysis tasks).

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 5:
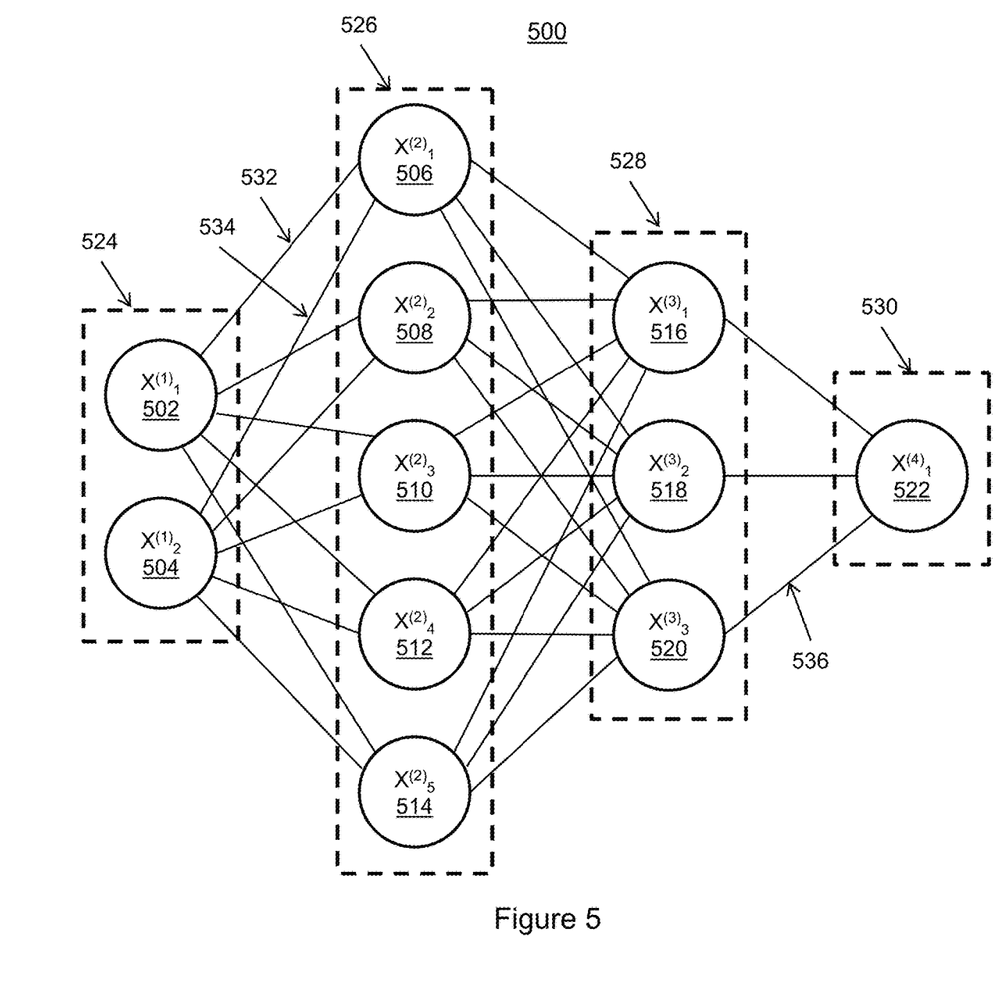
FIG. 5 shows an exemplary artificial neural network that may be used to implement one or more embodiments.

FIG. 5 shows an embodiment of an artificial neural network 500, in accordance with one or more embodiments.

Alternative terms for "artificial neural network" are "neural network", "artificial neural net" or "neural net". Machine learning networks described herein, such as, e.g., the machine learning based models applied at steps 206 and 208 of FIG. 2, may be implemented using artificial neural network 500.

The artificial neural network 500 comprises nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522, it is also possible that the first node 502-522 and the second node 502-522 are identical. For example, in FIG. 5, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 can be arranged in layers 524-530, wherein the layers can comprise an intrinsic order introduced by the edges 532, 534, . . . , 536 between the nodes 502-522. In particular, edges 532, 534, . . . , 536 can exist only between neighboring layers of nodes. In the embodiment shown in FIG. 5, there is an input layer 524 comprising only nodes 502 and 504 without an incoming edge, an output layer 530 comprising only node 522 without outgoing edges, and hidden layers 526, 528 in-between the input layer 524 and the output layer 530. In general, the number of hidden layers 526, 528 can be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number can be assigned as a value to every node 502-522 of the neural network 500. Here, $x^{(n)}_i$ denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 can comprise a weight being a real number, in particular, the weight is a real number within the interval [−1, 1] or within the interval [0, 1]. Here, $w^{(m,n)}_{i,j}$ denotes the weight of the edge between the i-th node 502-522 of the m-th layer 524-530 and the j-th node 502-522 of the n-th layer 524-530. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 502-522 of the (n+1)-th layer 524-530 can be calculated based on the values of the nodes 502-522 of the n-th layer 524-530 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 524 are given by the input of the neural network 500, wherein values of the first hidden layer 526 can be calculated based on the values of the input layer 524 of the neural network, wherein values of the second hidden layer 528 can be calculated based in the values of the first hidden layer 526, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 530, wherein f' is the first derivative of the activation function, and $y^{(n+1)}_j$ is the comparison training value for the j-th node of the output layer 530.

Figure 6:
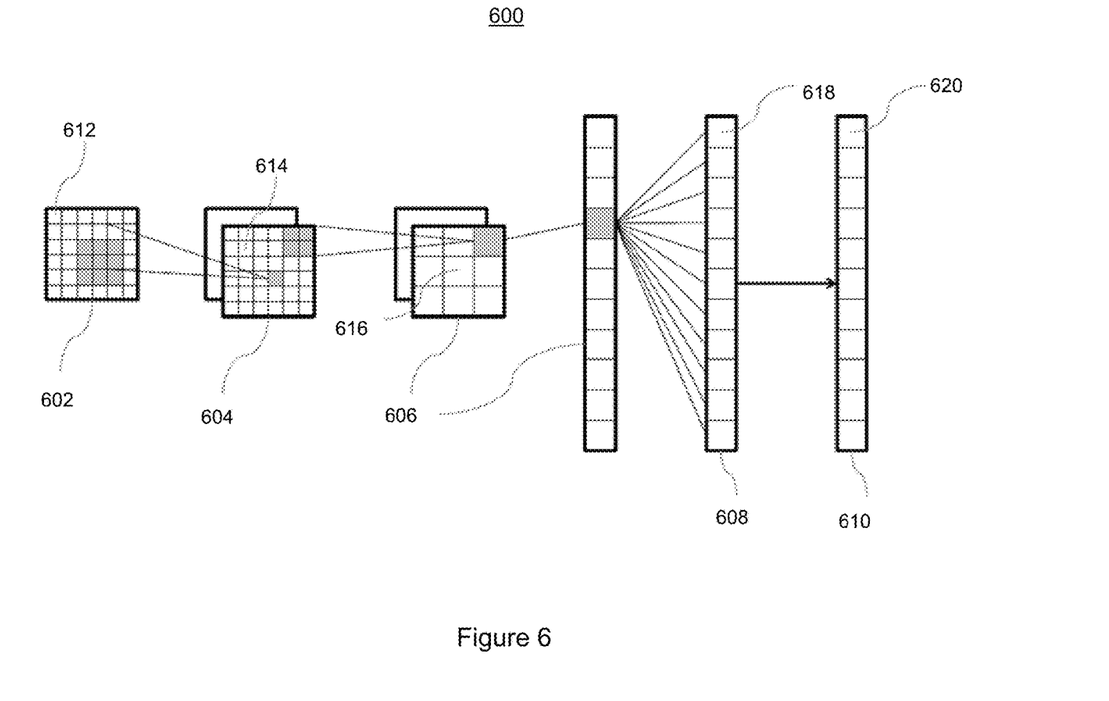
FIG. 6 shows a convolutional neural network that may be used to implement one or more embodiments.

FIG. 6 shows a convolutional neural network 600, in accordance with one or more embodiments. Machine learning networks described herein, such as, e.g., the machine learning based models applied at steps 206 and 208 of FIG. 2, may be implemented using convolutional neural network 600.

In the embodiment shown in FIG. 6, the convolutional neural network comprises 600 an input layer 602, a convolutional layer 604, a pooling layer 606, a fully connected layer 608, and an output layer 610. Alternatively, the convolutional neural network 600 can comprise several convolutional layers 604, several pooling layers 606, and several fully connected layers 608, as well as other types of layers. The order of the layers can be chosen arbitrarily, usually fully connected layers 608 are used as the last layers before the output layer 610.

In particular, within a convolutional neural network 600, the nodes 612-620 of one layer 602-610 can be considered to be arranged as a d-dimensional matrix or as a d-dimensional image. In particular, in the two-dimensional case the value of the node 612-620 indexed with i and j in the n-th layer 602-610 can be denoted as $x^{(n)}_{[i,j]}$. However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $x^{(n)}_k$ of the nodes 614 of the convolutional layer 604 are calculated as a convolution $x^{(n)}_k = K_k * x^{(n-1)}$ based on the values $x^{(n-1)}$ of the nodes 612 of the preceding layer 602, where the convolution * is defined in the two-dimensional case as $$x^{(n)}_k[i,j] = (K_k * x^{(n-1)})[i,j] = \Sigma_{i'} \Sigma_{j'} K_k[i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels can be interpreted as adding a further dimension (denoted as "depth" dimension), so that the nodes 614 of the convolutional layer 604 are arranged as a (d+1)-dimensional matrix. If the nodes 612 of the preceding layer 602 are already arranged as a (d+1)-dimensional matrix comprising a depth dimension, using a plurality of kernels can be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data can exploited by enforcing a local connectivity pattern between nodes of adjacent layers, in particular by each node being connected to only a small region of the nodes of the preceding layer.

In embodiment shown in FIG. 6, the input layer 602 comprises 36 nodes 612, arranged as a two-dimensional 6×6 matrix. The convolutional layer 604 comprises 72 nodes 614, arranged as two two-dimensional 6×6 matrices, each of the two matrices being the result of a convolution of the values of the input layer with a kernel. Equivalently, the nodes 614 of the convolutional layer 604 can be interpreted as arranges as a three-dimensional 6×6×2 matrix, wherein the last dimension is the depth dimension.

A pooling layer 606 can be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 can be calculated based on the values $x^{(n-1)}$ of the nodes 614 of the preceding layer 604 as $$x^{(n)}[i,j] = f(x^{(n-1)}[id_1, jd_2], \ldots, x^{(n-1)}[id_1 + d_1 - 1, jd_2 + d_2 - 1])$$

In other words, by using a pooling layer 606, the number of nodes 614, 616 can be reduced, by replacing a number d1·d2 of neighboring nodes 614 in the preceding layer 604 with a single node 616 being calculated as a function of the values of said number of neighboring nodes in the pooling layer. In particular, the pooling function f can be the max-function, the average or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 6, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 can be characterized by the fact that a majority, in particular, all edges between nodes 616 of the previous layer 606 and the nodes 618 of the fully-connected layer 608 are present, and wherein the weight of each of the edges can be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 can differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 600 can be trained based on the backpropagation algorithm. For preventing overfitting, methods of regularization can be used, e.g. dropout of nodes 612-620, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 2. Certain steps or functions of the methods and workflows described herein, including one or more of the steps or functions of FIG. 2, may be performed by a server or by another processor in a network-based cloud-computing system. Certain steps or functions of the methods and workflows described herein, including one or more of the steps of FIG. 2, may be performed by a client computer in a network-based cloud computing system. The steps or functions of the methods and workflows described herein, including one or more of the steps of FIG. 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
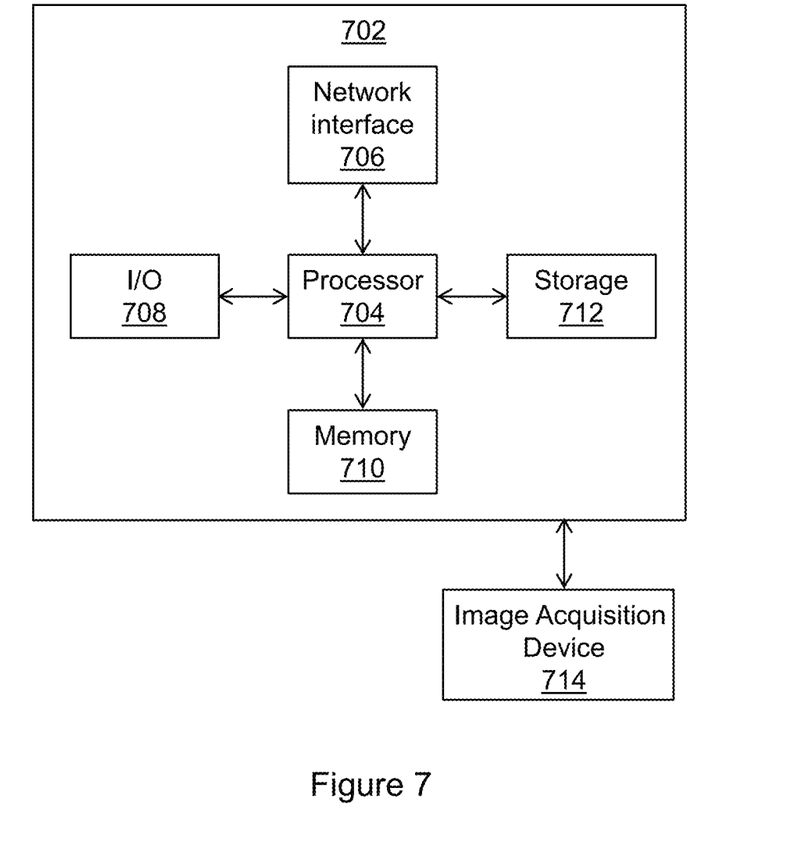
FIG. 7 shows a high-level block diagram of a computer that may be used to implement one or more embodiments.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 2 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 2. Accordingly, by executing the computer program instructions, the processor 704 executes the method and workflow steps or functions of FIG. 2. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems and apparatus discussed herein may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method comprising:
   receiving an input medical image in a first modality;
   generating a synthetic image in a second modality from the input medical image;
   upsampling the synthetic image to increase a resolution of the synthetic image;
   generating an output image to simulate image processing of the upsampled synthetic image; and
   outputting the output image,
   wherein:
   the input medical image comprises annotations,
   generating a synthetic image in a second modality from the input medical image comprises translating the annotations to correspond to the synthetic image, and
   upsampling the synthetic image to increase a resolution of the synthetic image comprises resampling the translated annotations to the resolution of the upsampled synthetic image.

2. The computer implemented method of claim 1, wherein upsampling the synthetic image to increase a resolution of the synthetic image comprises:
   performing a first upsampling of the synthetic image to increase a one-dimensional resolution of the synthetic image in a head-feet dimension using a first trained machine learning based model; and
   performing a second upsampling of the synthetic image to increase a two-dimensional resolution of the synthetic image using a second trained machine learning based model.

3. The computer implemented method of claim 1, wherein generating an output image to simulate image processing of the upsampled synthetic image comprises:
   generating the output image using a trained machine learning based model.

4. The computer implemented method of claim 3, wherein the trained machine learning based model is trained using unpaired training images.

5. The computer implemented method of claim 1, wherein generating a synthetic image in a second modality from the input medical image comprises:
   segmenting an anatomical object of interest from the input medical image;
   masking regions of the input medical image outside of the segmented anatomical object of interest; and
   generating the synthetic image from the masked input medical image.

6. The computer implemented method of claim 1, wherein the first modality is CT (computed tomography) and the second modality is x-ray, and wherein generating a synthetic image in a second modality from the input medical image comprises:
   generating a DRR (digitally reconstructed radiograph) from the input medical image.

7. The computer implemented method of claim 1, further comprising:
   training a machine learning based model for performing a medical imaging analysis task based on the output image.

8. A computer implemented method comprising:
receiving an input medical image in a first modality;
generating a synthetic image in a second modality from the input medical image;
upsampling the synthetic image to increase a resolution of the synthetic image;
generating an output image to simulate image processing of the upsampled synthetic image;
outputting the output image;
generating one or more additional synthetic images in the second modality from the input medical image; and
repeating the upsampling, the generating the output image, and the outputting steps for each respective additional synthetic image of the one or more additional synthetic images using the respective additional synthetic image as the synthetic image to generate a plurality of output images.

9. The computer implemented method of claim 8, wherein upsampling the synthetic image to increase a resolution of the synthetic image comprises:
performing a first upsampling of the synthetic image to increase a one-dimensional resolution of the synthetic image in a head-feet dimension using a first trained machine learning based model; and
performing a second upsampling of the synthetic image to increase a two-dimensional resolution of the synthetic image using a second trained machine learning based model.

10. An apparatus comprising:
means for receiving an input medical image in a first modality;
means for generating a synthetic image in a second modality from the input medical image;
means for upsampling the synthetic image to increase a resolution of the synthetic image;
means for generating an output image to simulate image processing of the upsampled synthetic image; and
means for outputting the output image,
wherein:
the input medical image comprises annotations,
the means for generating a synthetic image in a second modality from the input medical image comprises means for translating the annotations to correspond to the synthetic image, and
the means for upsampling the synthetic image to increase a resolution of the synthetic image comprises means for resampling the translated annotations to the resolution of the upsampled synthetic image.

11. The apparatus of claim 10, wherein the means for upsampling the synthetic image to increase a resolution of the synthetic image comprises:
means for performing a first upsampling of the synthetic image to increase a one-dimensional resolution of the synthetic image in a head-feet dimension using a first trained machine learning based model; and
means for performing a second upsampling of the synthetic image to increase a two-dimensional resolution of the synthetic image using a second trained machine learning based model.

12. The apparatus of claim 10, wherein the means for generating an output image to simulate image processing of the upsampled synthetic image comprises:
means for generating the output image using a trained machine learning based model.

13. The apparatus of claim 12, wherein the trained machine learning based model is trained using unpaired training images.

14. The apparatus of claim 10, wherein the means for generating a synthetic image in a second modality from the input medical image comprises:
means for segmenting an anatomical object of interest from the input medical image;
means for masking regions of the input medical image outside of the segmented anatomical object of interest; and
means for generating the synthetic image from the masked input medical image.

15. A non-transitory computer readable medium storing computer program instructions, the computer program instructions when executed by a processor cause the processor to perform operations comprising:
receiving an input medical image in a first modality;
generating a synthetic image in a second modality from the input medical image;
upsampling the synthetic image to increase a resolution of the synthetic image;
generating an output image to simulate image processing of the upsampled synthetic image; and
outputting the output image,
wherein:
the input medical image comprises annotations,
generating a synthetic image in a second modality from the input medical image comprises translating the annotations to correspond to the synthetic image, and
upsampling the synthetic image to increase a resolution of the synthetic image comprises resampling the translated annotations to the resolution of the upsampled synthetic image.

16. The non-transitory computer readable medium of claim 15, wherein upsampling the synthetic image to increase a resolution of the synthetic image comprises:
performing a first upsampling of the synthetic image to increase a one-dimensional resolution of the synthetic image in a head-feet dimension using a first trained machine learning based model; and
performing a second upsampling of the synthetic image to increase a two-dimensional resolution of the synthetic image using a second trained machine learning based model.

17. The non-transitory computer readable medium of claim 15, wherein the first modality is CT (computed tomography) and the second modality is x-ray, and wherein generating a synthetic image in a second modality from the input medical image comprises:
generating a DRR (digitally reconstructed radiograph) from the input medical image.

18. The non-transitory computer readable medium of claim 15, the operations further comprising:
training a machine learning based model for performing a medical imaging analysis task based on the output image.

19. A non-transitory computer readable medium storing computer program instructions, the computer program instructions when executed by a processor cause the processor to perform operations comprising:
receiving an input medical image in a first modality;
generating a synthetic image in a second modality from the input medical image;
upsampling the synthetic image to increase a resolution of the synthetic image;

generating an output image to simulate image processing of the upsampled synthetic image;

outputting the output image;

generating one or more additional synthetic images in the second modality from the input medical image; and repeating the upsampling, the generating the output image, and the outputting operations for each respective additional synthetic image of the one or more additional synthetic images using the respective additional synthetic image as the synthetic image to generate a plurality of output images.

20. An apparatus comprising:

means for receiving an input medical image in a first modality;

means for generating a synthetic image in a second modality from the input medical image;

means for upsampling the synthetic image to increase a resolution of the synthetic image;

means for generating an output image to simulate image processing of the upsampled synthetic image;

means for outputting the output image;

means for generating one or more additional synthetic images in the second modality from the input medical image; and means for repeating the means for upsampling, the means for generating the output image, and the means for outputting for each respective additional synthetic image of the one or more additional synthetic images using the respective additional synthetic image as the synthetic image to generate a plurality of output images.

* * * * *

UNITED STATES PATENT AND TRADEMARK OFFICE
CERTIFICATE OF CORRECTION

PATENT NO. : 11,908,047 B2
APPLICATION NO. : 17/249735
DATED : February 20, 2024
INVENTOR(S) : Boris Mailhe et al.

Page 1 of 1

It is certified that error appears in the above-identified patent and that said Letters Patent is hereby corrected as shown below:

On the Title Page

After Item (65) please add:
Related U.S. Application Data
(60) Provisional application No. 63/041,372, filed on Jun. 19, 2020.

Signed and Sealed this
Eighth Day of October, 2024

Katherine Kelly Vidal
*Director of the United States Patent and Trademark Office*